(12) United States Patent
Wallach et al.

(10) Patent No.: US 6,479,655 B1
(45) Date of Patent: Nov. 12, 2002

(54) TNF RECEPTOR PROMOTER

(75) Inventors: David Wallach, Rehovot (IL); Oliver Kemper, Bockenheim (DE)

(73) Assignee: Yeda Research and Development Co. Ltd., Rehovot (IL)

( * ) Notice: Subject to any disclaimer, the term of this patent is extended or adjusted under 35 U.S.C. 154(b) by 1263 days.

(21) Appl. No.: 08/600,203

(22) Filed: Feb. 12, 1996

Related U.S. Application Data

(63) Continuation of application No. 08/178,564, filed on Jan. 7, 1994, now abandoned.

(30) Foreign Application Priority Data

Jan. 10, 1993 (IL) .................................................. 104355

(51) Int. Cl.[7] .............................................. C07H 21/04
(52) U.S. Cl. ..................... 536/24.1; 536/24.1; 536/23.1
(58) Field of Search ............................... 536/24.1, 23.1; 935/6

(56) References Cited

FOREIGN PATENT DOCUMENTS

| EP | 0231624 | 8/1987 |
|---|---|---|
| EP | 0417563 | 3/1991 |
| EP | 0433900 | 6/1991 |

OTHER PUBLICATIONS

TA Brown (1990) Gene Cloning, An Introduction pp 153–177.*
L–H Guo et al (1983) Nucleic Acids Research 5521–5540.*
JD Watson et al (1992) Recombinant DNA pp 153–159.*
A Bielinska et al (1990) Science 250:997–1000.*
P Fuchs et al (1992) Genomics 13:219–224.*
VM Kähäri et al (1990) J. Biol. Chem. 265:9485–9490.*
Derre et al., *The gene for the type 1 tumor necrosis factor receptor (TNF–R1) is localized on band 12p13*, Human Genetics, vol. 87, pp. 231–233, 1991.
Fuchs et al., *Structure of the Human TNF Receptor 1 (p60) Gene (TNRF1) and Localization to Chromosome 12p13*, Genomics, vol. 13, pp. 219–224, 1992.
Kemper et al., *Cloning and partial characterization of the promoter for the human p55 tumor necrosis factor (TNF) receptor*, Gene, vol. 134, pp. 209–216, 1993.

* cited by examiner

*Primary Examiner*—Dave T. Nguyen
*Assistant Examiner*—Quang Nguyen
(74) *Attorney, Agent, or Firm*—Browdy and Neimark

(57) ABSTRACT

A promoter sequence of the human p55 TNF-R gene is provided. Also provided are sequence motifs and motif regions contained within the promoter sequence. Methods for preparing these motifs or motif regions and their use in the modulation of TNF function are also provided.

4 Claims, 4 Drawing Sheets

FIG. 1

```
        NF-kB  E2aE-Cβ
-809    GATCAGTAGTAATTCCCAAGAAAAGAGGAGACTAGGAGAGGCTAGTGAAGAACTCTGGAGTAAAGGGGAGGATT

-739    ACTAAGGGACATGGAGTACCTATCATGTCGGACGCTTATCTATATCTCTCCCATCTGAACACAAATCCTT
                                                                        CAATT
-669    ACAGGAACCCCAGGAGACAGGTTATCTCCACTCTGCAAATTGGAAAACAGATCCAGACAGTTCAGTTAT
                                                                         CAATT
-599    GTGTCTGAGAAGTTCATTTGTGTCCAAGACACATTCTTAGCTAAAAAGCTAAGCATTCTGAATTGGAA

-529    CCCAGAGAATTTGACTCCCAGACTCTGGATCTTTTCACTGCTGTGATCCATCTGGGAAAGCTAGTGATG
                                                             CAATT    AP-2
-459    TGGGCAAGGGCTTATTGCCCCTTGGTGTTGGGAGTGGTCGGATTGGTGGGTTGGGGCACAAGGC
                                                                   JCV...SP-1...
                                                  TATA?            S1 HS
-389    AGCCAGATCTGGGACTCCTGTGCTTGTGACTGGACTACAAAGAGTTAAAGAACGTTGGGCCTCCTCCTCC
         JCV...SP-1
-319    CGCCTCCTGTGGCCTCTCCTCCAGCTCTTCCTGTCCCGCTGTTGCAACACTGCCTCACTCTTCCCCTCC
        ...JCV       "AP-1"        ↓↓       →    ↓↓      →      ↓    JCV...
-249    CACCTTTCTCTCCCCCTCTGCTTTAATTTTCTCAGAATTCTCTGGACTGAGGCTCCAGTTCTGGCCT

-179    TTGGGGTTCAAGATCACTGGGACCAGGCCGTGATCTCTATGCCCGAGTCTCAACCCTCAACTGTCACCCC
                                                              NF-kB
-109    AAGGCACTTGGGACGTCCTGGACAGACCGAGTCCCGGAAGCCCCAGCACTGCCGCTGCCACACTGCCCT

-39    GAGCCCAAAATGGGGAGTGAGAGGCCATAGCTGTCTGGCATGGCCCTCCCACCGTGCCTGCCTGACCTGCTGC
                                                           MetGlyLeuSerThrValProAspLeuLeuL
 +32    TGCCACTGGTGAGACCAGGACAAAGGGAAGAGTGGGCGTGGGCGAGGCACCTTCCGGCTGGCGTGGG
        euProLeu            JCV       NRE
+102    CCCTCTCCGGGAGGGGCGAGCCTCTCCTGCCCGGCCTGGTCCTGGCGCCAGTCAGGCCTGCAGGTCC
                                                              NF-kB
+172    TAACCTCAGCCACTGCCAGTGTGGGGTTCCCCATTCATCCGCCTTTTGGAGTAGGGCCTGCGCTGAGGCA

+242    GGGGAATGGGGAGAAGTTTGAAAGGGAGAGAGTAAAAGGAAGCCCTGCCCCTGACACGCGGTGGAAGTTTGT
        SP-1                                                         JCV       SP-1
+313    GGGCGGCCAAGGGAATGTGGGCAGGAGTAGGCCCAGGTGGGGCAGATTTGGCGGGGAAAAGAAGGGAGT

+384    GGGAGTAGGAAGATTAGCGCTCGGGAGTCCAGACGGTTCTGAATTC
```

TNF RECEPTOR PROMOTER

This application is a continuation of application Ser. No. 08/178,564, filed Jan. 7, 1994, now abandoned.

FIELD OF THE INVENTION

The present invention relates to a promoter sequence for the p55 tumor necrosis factor receptor (TNF-R), to its preparation and use.

BACKGROUND OF THE INVENTION

TNF is a multifunctional pro-inflammatory cytokine which affects a wide range of cellular functions. On the one hand, TNF is involved in the protection of the organism, but on the other hand, when over-produced, it can play a major pathogenic role in several diseases. TNF is known to be involved in inflammatory processes and to be a mediator of the damage to tissues in septic shock[1], graft-versus-host reactions[2] and in rheumatic diseases[3].

TNF exerts these effects by binding to two distinct cell surface receptors, which differ in size (about 55 and 75 kDa) and possess structurally dissimilar intracellular domains, suggesting that they signal differently[4-11]. Almost all cells express TNF receptors (TNF-Rs), yet the amounts and relative proportions of the two receptors vary in different cell types. These variations are in part developmentally controlled; they are related to the phenotype of the cell and its state of differentiation, and in part can be induced transiently by cytokines and immune stimulatory components of pathogens[12-22]. Studies of the function of the two TNF-Rs indicate that they have different yet interacting activities[23-28], and that their activity level may be correlated to the extent of their expression by the cell[29-30]. These findings imply that the mechanisms which affect the amounts and relative proportion of the two TNF-Rs can have significant influence both on the nature and the extent of the cellular response to TNF and thus constitute important determinants of the physiological as well as pathological manifestations of the funtion of this cytokine.

In order to inhibit the deleterious effects of TNF, ways were sought which would interfere with the binding of TNF to its receptors. Thus neutralizing antibodies to TNF were raised (EP 186 833). Another approach to the inhibition of the action of TNF was the provision of soluble TNF receptors which compete with the cell surface TNF-Rs for the binding of TNF (EP 308 378 and EP 398 327).

Since binding to its receptors is required for TNF in order to exert its action, if less or no cell surface receptors are expressed, it should be possible to decrease or inhibit the deleterious effects of TNF. By the same token, it may be desired in certain cases to augment the beneficial action of TNF and in such a case this could possibly be achieved by increasing the amount of cell surface receptors expressed.

SUMMARY OF THE INVENTION

The present invention provides a promoter sequence of the human p55 TNF-R gene which is located upstream of the 5' end of the gene and is contained within a 976 bp sequence.

The invention in a preferred embodiment provides the NheI-PstI fragment of the full length genomic clone encoding the human p55 TNF-R.

The invention also provides the NheI-EcoRI fragment of the above NheI-PstI fragment.

The invention further provides the BglII-EcoRI fragment of the above NheI-EcoRI fragment.

A promoter sequence according to the present invention may be employed for diagnosing either inherited or acquired mutations in the promoter region which contribute to the pathology of diseases.

In another aspect, the invention provides sequence motifs present in the above described promoter sequences. Such motifs have been shown to bind certain transcription factors which could be necessary for promoter activity and might be involved in regulation of this promoter.

The motifs may be prepared by deletion of the unwanted sequences upstream and/or downstream of the desired motif in the full sequence, i.e., by employing restriction enzymes to cut the full promoter sequence to arrive at the desired motif, and the resulting motif can then be inserted into a vector together with suitable control sequences and other conventional means required in order to obtain a vector which, on insertion into a suitable prokaryotic strain is capable of expression of the desired motif on culturing of the strain.

The motif thus obtained can be used to screen, e.g., a human genomic library or a cDNA library for factors, e.g., transcription factors, binding thereto. Once these factors have been isolated, purified and identified by any conventional means, their inhibition should inhibit TNF-R formation, while their increased production should cause enhanced TNF-R expression thereby leading to the desired effect of modulating TNF function, i.e. inhibition or enhancement of TNF binding to its receptors.

Since the amount of specific transcription factors present in vivo is not unlimited, inhibition of TNF-R expression a n d consequent inhibition of deleterious TNF effects could also be achieved by the expression of a large number of motifs or motif regions. These will compete with promoters containing such motifs or motif regions for binding of the transcription factors. A "motif region" comprises the motif itself together with sequences flanking it on both sides, or several motifs connected by parts of the whole promoter sequence and flanked on both sides by sequence parts.

The present invention also provides pharmaceutical compositions comprising a sequence motif according to the invention.

In another aspect, the invention provides pharmaceutical compositions comprising a motif region according to the invention.

DESCRIPTION OF THE DRAWINGS

FIG. 1 shows the nucleotide sequence (SEQ ID NO:1) of the p55 TNF-R gene 5' flanking sequence, the first exon and part of the first intron. The A of the ATG translation start is defined as +1. Transcription start sites, as determined by S1 nuclease mapping (FIG. 3) are indicated by arrows. Potential transcription factor binding sites are indicated by lines above the sequence. The consensus intron donor site is underlined.

DETAILED DESCRIPTION OF THE INVENTION

Figure 2:
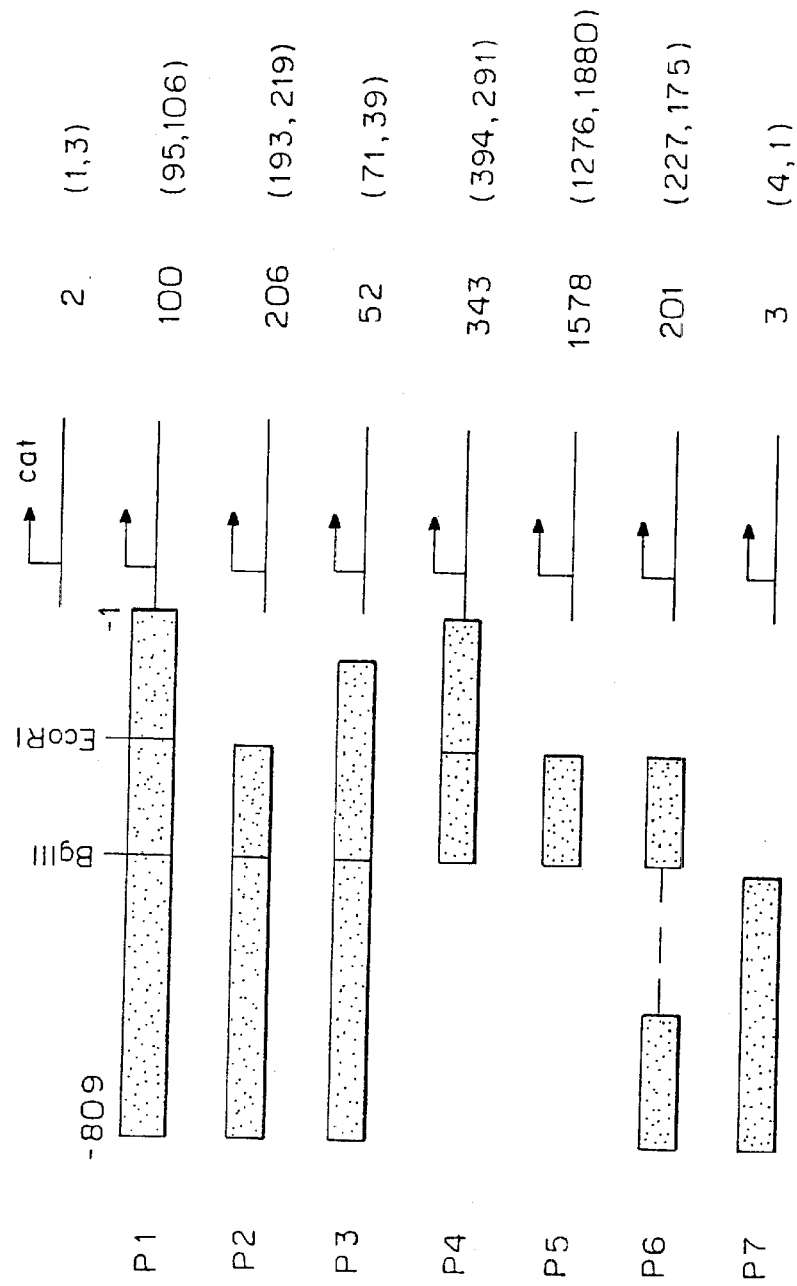
FIG. 2 shows the activity of p55 TNF-R promoter constructs in HeLa cells. Left side: diagrammatic presentation of promoter constructs. The numbers above the scheme correspond to nucleotide numbers as in FIG. 1. The stippled line in construct P6 represents a deletion. Right side: relative values of CAT activity obtained from the constructs after transient transfection, where 100 corresponds to 4% acetylation of CAT.

A full length genomic clone of the human p55 TNF-R was isolated from a human genomic library. The clone was found to extend 809 base pairs (bp) upstream of the translation start site of the TNF-R. A 1.16 kb (NheI-PstI) fragment of this clone was subcloned and several deletion constructs thereof prepared.

The 1.16 kb fragment has promoter activity, shown by its ability to drive effective expression of the CAT reporter gene in both human HeLa cells and mouse A9 cells. Deletion constructs of this clone showed that promoter activity was confined to a 178 bp BglII-EcoRI fragment which included most of the transcription start points. Further analysis showed that a minimal promoter of 69 bp still exhibits activity.

S1 nuclease digestion analysis of the RNA of HeLa and U 937 cells with DNA probes revealed in both cell lines multiple start sites of transcription. The locations of these start sites were identical with all probes used.

It was found that the promoter sequence according to the present invention resembles promoters of house-keeping genes (e.g., the hypoxanthene phosphoribosyltransferase[61], the EGF receptor[62], the NGF receptor[60] or the p55 interleukin-1 receptor[63]. It is devoid of a TATA box and of a CCAAT motif and is relatively rich in G and C residues in its 3' end. There is an even higher content of G and C resides in the, proximally located, 5' end of the first intron. This region is also rich in the dinucleotide couple CG, which may allow for differentiation-related changes in the promoter activity as a function of the extent of methylation of these nucleotides.

The above features are consistent with the multiplicity of transcription start sites for the p55 TNF receptor gene. They are also consistent with the current knowledge of the way in which this gene is regulated: showing constitutive expression in a variety of different cells, e.g., fibroblasts[5,6], including some in which the receptor protein is barely detectable, e.g., in the U937 cells (compare[9] and[5]), at an extent which may vary in correlation with their differentiation state[22]. In contrast to these house-keeping characteristics of the gene which encodes the p55 TNF receptor, TNF itself is formed transiently by only a few cell types in strict dependence on inducing agents[64]. Accordingly, the promoters of both the TNFα and TNFβ genes display features characteristic of inducible genes[65], (reviewed in:[66]). These differences in regulation of the expression of TNF and its receptors are consistent with the physiological role of TNF. Serving as an "alert signal", particularly during invasion of pathogens, the formation of this cytokine would be restricted to the time of need, while the ability to respond to it, which fully depends on the expression of TNF receptors, would be constantly maintained. One would expect the receptors for cytokines, in general, to be expressed in a less restricted manner than the cytokines themselves, both with regard to their time of expression and to the type of cell in which it occurs. The promoter for the NGF receptor, whose extracellular domain is evolutionarily related to those of the TNF receptors also displays. house-keeping features[60]. Like the promoter for the p55 TNF-R, it lacks CCAAT and TATA elements, has multiple transcription start sites and is rich in G/C residues. Yet in other respects the architecture of the two promoters is quite different. For example, while in the NGF receptor gene the 5' flanking sequence is very rich in G/C residues (71%), G/C richness in the p55 TNF-R is confined to the region downstream of the transcription initiation sites, and is particularly notable at the 5' end of the first intron (70% G/C, bp 40–200).

As stated above, some known receptors have housekeeping features. The genes of a number of known receptors are modulated also transiently, and contain the regulatory elements necessary for such regulation (e.g., the IL-2 receptor alpha chain[67]). Examination of the promoter sequence of the p55 receptor reveals sequence motifs which may, similarly, allow response to transcriptional factors which are affected by inducing agents, including consensus sequences for AP2 and NF-kB. These regulatory elements may allow for induced transient changes, superimposed on the pattern of constitutive expression of the receptor, perhaps by effects of certain cytokines which are formed at sites of inflammation. Transient changes in TNF binding, in part due to altered expression of the p55 TNF-R, were observed in a number of studies[12-29], yet whether these changes occur at the transcriptional, or on post-transcriptional levels remains to be established.

Among the putative motifs discerned in the promoter region, the sequence GGCCTCCTCCTCC(nucleotides 478–490 and 501–513 of SEQ ID NO:1), which is found at bp −332 and −309, is of particular interest. The sequence TCCTCCTCC within this motif occurs also in the promoter of the EGF receptor and is essential for its promoter activity; it constitutes a site of Nuclease S1 hypersensitivity, and binds an SP-1 like factory. The region surrounding these elements shows an overall C/T abundance—a feature that has been implicted with DNAse hypersensitivity and sites of active transcription in the chromosome. It is therefore assumed that this region is necessary also for the promoter activity of the p55 TNF receptor.

The present invention also concerns pharmaceutical compositions comprising a pharmaceutically acceptable carrier and a sequence motif or motif region of the invention. These compositions may be used against any disease caused by an excess of TNF, either endogenously present or exogenously administered. Examples of diseases are septic shock, graft-versus-host reactions, rheumatic diseases and other autoimmune diseases.

The way of administration can be via any of the accepted modes of administration for similar agents and will depend on the condition to be treated, e.g., intravenously, intramuscularly, subcutaneously, by local injection or by topical application, as the case may require.

The pharmaceutical compositions of the invention are prepared for administration by mixing the sequence motif or motif region with physiologically acceptable carriers, stabilizers and excipients, and prepared in dosage form, e.g., by lyophilization in dosage vials. The amount of active compound to be administered will depend on the route of administration, the disease to be treated and the condition of the patient. Local injection, for instance, will require a lower amount on a body weight basis than will, e.g., intravenous infusion.

The invention is illustrated by the following non-limiting examples:

Cell Lines and Culture Conditions

The human HeLa[31] and mouse A9[32] cell lines were grown in Dulbecco's modified Eagle's medium. The human histiocytic cell line U937[33] was grown in RPMI 1640 medium. Both media were supplemented with 10% fetal calf serum, 100 units/ml penicillin and 100 g/ml streptomycin. The cell cultures were maintained in a 5% $CO_2$ atmosphere at 37° C.

EXAMPLE 1

Cloning and Sequencing

The cloning and several features of the full-length genomic clone encoding the p55TNF-R gene have been described[34]. A 1.16 kb NheI-PstI fragment of this clone comprising part of the first intron of the p55 TNF-R gene, the first exon, 5' flanking gene sequences and 180 bp of the left arm of the lambda phage, was subcloned into the pBluescript vector digested with XbaI and PstI. This construct was termed NP. Partial deletions of this construct were made using the internal restriction sites EcoRI and BglII. A 3' deletion construct, NR was created by digesting the NP construct with EcoRI, thereby excising bp−211 to +168 of the insert (numbers start at the ATG translation start, see in FIG. 1), followed by isolation of the 3.69 kb vector fragment and religation. Another 3' deletion construct, NB, was created by digesting the NP construct with BglII and EcoRI, thereby excising bp−384 to +168 of the insert, blunting the ends with Klenow polymerase and, after isolating the 3.55 kb vector fragment, carrying out religation. A 5' deletion construct, BP, was obtained by cloning the 0.54 kb BglII-PstI fragment of the genomic phage (from bp−384 to +168) into the pBluescript vector digested with Bam HI and PstI. The promoter fragments were excised from pBluescript with SacI and SalI and cloned into the CAT expression vector PGEMCAT (a generous gift from Dr. J. Chebath[35]) digested with SacI and SalI. DNA sequencing was performed using the chain termination method[36]. The above constructs were sequenced using the T3 and T7 primers of pBluescript. Additional sequence information was obtained from within the cloned sequence using the oligonucleotide primers 5' CAATTCAGAATGCTTAGCTTT (SEQ ID NO:4) and 5' GATCAGTAAATTCCCAAGAAAGA(123 of SEQ ID NO:1 ) The latter oligonucleotide which starts at bp −809 in FIG. 1 was also used in a PCR reaction together with the T3 primer of the pBluescript vector to generate promoter fragments which are not linked to lambda phage sequences.

EXAMPLE 2

Promoter Activity of a 5' Sequence in the p55 TNF-R Gene

A full-length genomic clone of the p55 TNF-R was isolated from a human genomic library, using a partial cDNA clone of the receptor as a probe[34]. Sequence analysis of the 5' end of the clone showed that it extends 809 nucleotides upstream of the translation start site of the protein. Unlike the coding region[40], the 5' extending region seemed to be devoid of disruption by introns.

To determine whether the cloned sequence has promoter activity, a fragment extending from an NheI site within the left arm of the lambda phage to a PstI site at pos. +168 within the gene sequence, and parts of this fragment, were cloned into pBluescript. The sequence from the translation start codon ATG upstream (bp −809 to −1) was subcloned using PCR technique, and this sequence (P1) as well as deletions thereof were examined for expression of CAT activity by a transient transfection assay. As shown in FIG. 2, the full length fragment P1 drove effective expression of the CAT gene, in human HeLa cells.

Deletion of 206 bp from the 3' end of the fragment (construct P2) somewhat enhanced CAT expression. This increase may be related to the occurence of two ATG's followed by in-frame stop codons in the deleted region (at bp −141 and −31), which may inhibit efficient initiation of translation. Indeed, deletion of only 74 bp from the 3' end of P1, eliminating the stop codon for the 3' ATG codon in the leader, led to decreased CAT expression (construct P3). A significant increase was observed when 425 bp of the 5' end of P1 (construct P4) were deleted, suggesting the presence of a negative regulatory element in the deleted region. An even higher promoter activity was observed in deletion of both 5' 425 bp and 3' 206 bp sequences from P1 (construct P5). The internal deletion construct P6 (deletion of bp −663 to −379) showed the same activity as P2, suggesting that the negative regulatory element resides between bp −809 and −bp −663. The 425 bp 5' region itself is devoid of promoter activity (construct P7 in FIG. 2).

Further deletion analysis of the 178 bp fragment (construct P5 in FIG. 2) showed that its activity was unaffected by deleting bp −238 to −207, but decreased when more 3' sequences (up to bp −287) were deleted. Deletion of bp −306 to −207 however, fully abolished promoter activity. Therefore, the sequence between bp −287 to −238 has enhancing activity, while the core promoter resides upstream of bp −287. At the 5' end of the 178 bp fragment (P5 in FIG. 2), bp −385 to −355 could be deleted without effect, however further deletion up to bp −335 decreased promoter activity about five-fold. The boundaries of the core promoter are therefore between bp −355 to bp −287 (nucleotides 456–524 of SEQ ID NO:1).

EXAMPLE 3

Identification of Transcription Start Sites

Figure 3:
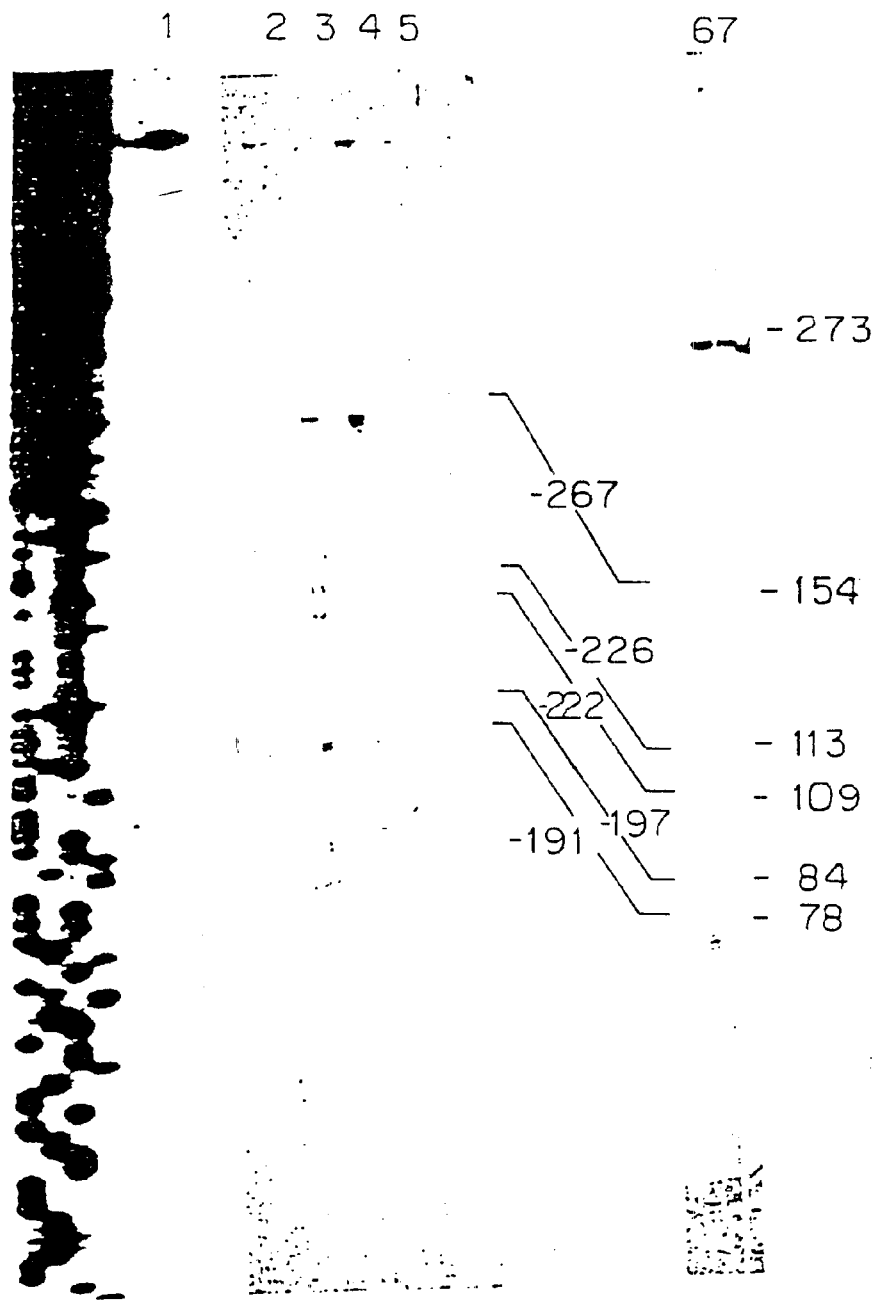
FIG. 3 shows the S1 nuclease mapping of transcription start sites of the p55 TNF receptor mRNA. Total RNA (100 μg) of HeLa, U937 or A9 cells, or 100 μg yeast tRNA was subjected to S1 nuclease analysis using 5' end-labeled ds (double-stranded) DNA probes. Arrows show protected fragments with their length given in nucleotides. The arrow at 273 bases shows undigested StyI probe. Corresponding bands obtained with different probes are connected by lines; the numbers at the lines indicate nucleotide positions as in FIG. 1. A sequencing ladder which served as a molecular weight marker (shown on the left A-C-G-T) was obtained using the genomic clone as a template and an oligonucleotide 5' GGTGACAGTTGAGGGTTGAGACT (SEQ ID NO:1 positioned 5 nucleotides upstream of the 3' end of the StyI-BglII probe. Lane 1: SmaI-BglII probe. Lane 2 to 5: S1 nuclease analysis using the SmaI-BglII probe. Lanes 6 and 7: S1 nuclease analysis using the StyI-BglII probe. Lanes 2 and 7: A9 RNA; Lanes 3 and 6: HeLa RNA; Lane 4: U937 RNA; Lane 5: yeast tRNA.
Figure 4A:
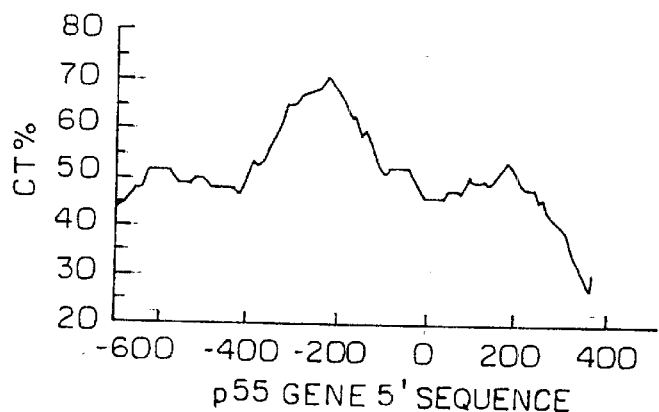
FIG. 4, in its upper part shows the nucleotide content of the p55 TNF-R gene 5' region. The percentage of G/C and C/T, and the frequency of the CpG dinucleotide couple, were calculated in a window of 200 nucleotides for the sequence presented in FIG. 1. The lower part of FIG. 4 shows a diagram of the 5' region. The arrows denote major transcription start sites.
Figure 4B:
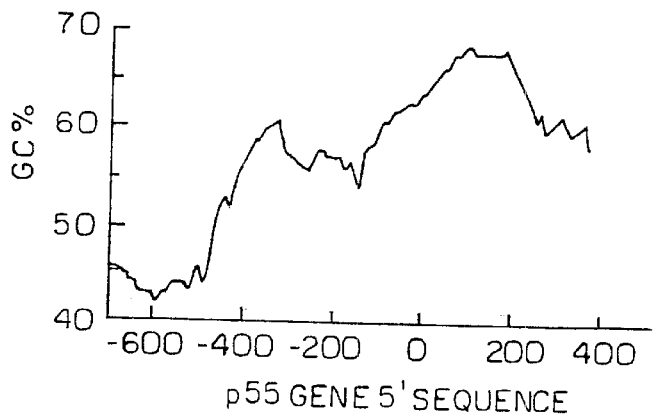
Figure 4C:
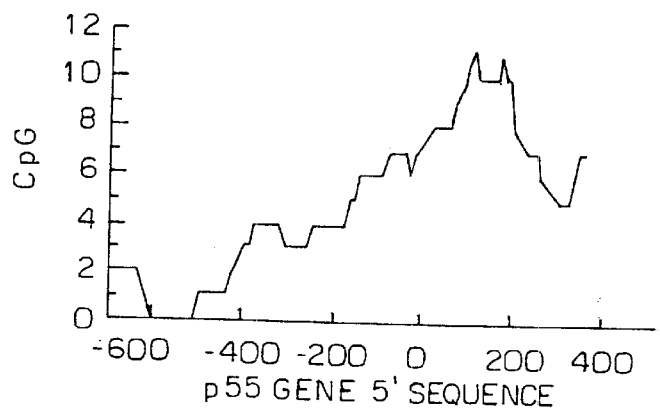
Figure 4D:
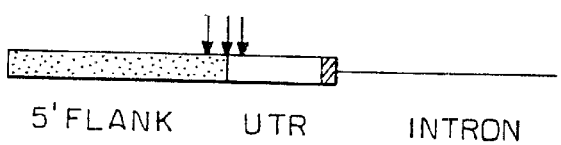

Transcription start sites of the p55 TNF-R gene were mapped by nuclease S1 protection assay using as DNA probes SmaI-BglII (310 bp) and StyI-BglII (274 bp) fragments of the 5' region of the p55 TNF receptor gene (5' $^{32}$P-end-labeled with T4 kinase at the SmaI and StyI sites). The probes were hybridized overnight at 52° C. to 100 μg of total RNA of HeLa, U937 or A9 cells, prepared according McDonald et al.[38] . After digestion for 1 hour at 37° C. with 200 units of S2 nuclease (Boehringer, Mannheim), the reaction products were precipitated by ethanol and analyzed on a 6% sequencing gel. As molecular weight marker served sequencing reations with an oligonucleotide primer 5' GGT-GACAGTTGAGGGTTGAGACT (SEQ ID NO:5) (complementary to bp −112 until −135). The 5' end of the primer lies 5 nucleotides upstream of the 5' end of the StyI probe (bp −110). S1 nuclease digestion analysis of the RNA of HeLa and U937 cells revealed multiple start sites of transcription in both cell lines, the most prominent one being at G-268 (FIG. 3 and arrows in FIG. 1, nucleotide numbers start at the translation start codon ATG, see FIG. 1). The locations of the start sites defined by a probe extending from −111 to 384 (StyI-BglII) were identical to those revealed by a probe extendng from −75 to −384 (SmaI-BglII). The locations of the start sites in HeLa and U937 cells were the same, with similar proportions of usage.

EXAMPLE 4
Transient Transfection and CAT Assay

HeLa and A9 cells were seeded into 9 cm dishes (500,000 cells/dish) and allowed to grow for 16 h. Ca PO$_4$ precipitates of DNA[39] were added to the medium and left on the cells for 12 h. The cells were then rinsed and allowed to grow in fresh medium for 48 h., rinsed again and scraped from the plates. Extracts were prepared and the CAT assay performed as described[39], using 20–25 µg protein per sample. Incubation times ranged between 4–12 h. Each assay was done at least twice, with duplicate transfections for each construct tested.

EXAMPLE 5
Sequence Motifs

The nucleotide sequence in the p55 TNF-R promoter, the first exon, and a part of the first intron is shown in FIG. 1. There is no TATA sequence in the proximity of any of the transcription start sites. The sequence TACAAA at position −354, which would serve, at low efficacy, as an alternative[41] is too remote from those sites to be functional.

It appears that the 5' end of the genomic clone lacks also a functional CCAAT motif. The sequence ATTGG, resembling a CCAAT box of the hsp70 gene promoter[42] occurs three times: at −631, −536 and −413. However, none of the three elements is located within 60 to 80 nucleotides of the transcription initiation sites which is the distance commonly found for CCAAT elements[43].

A computer search for sequence motifs for transcription factor binding sites, performed using the GCG program package[44], revealed several known motifs, including three consensus sites for NF-kB[45], at positions −804 (reverse), −73 (reverse) and −192; one site for the transcription factor AP-2[46] at −407, and an AP-1-like sequence[47] at −235. The core sequence of the ubiquitous transcription factor SP-1, GGCGGG[48] or CCGCCC[49], is found at positions −321, 313 and 364. However, none of these potential SP-1 binding sites fully matches the consensus sequence, G/T G/A GGCG G/T G/A G/A C/T (SEQ ID NO:6) proposed by Briggs et al.[50]. The putative SP-1 site at position −321 is flanked by two nuclease S1 hypersensitivity consensus sequences (S1 HS[51]). The sequence downstream of the minor start site at adenosine −210 (ATTCTCTGGACT) (nucleotides 600–611 of SEQ ID NO:1), shows high homology to the corresponding sequence in the "initiator" motif, initially defined in the lymphocyte-specific terminal deoxynucleotidyltransferase gene (ATTCTGGGAGAC) (SEQ ID NO:7)[52]. However, the sequence upstream of this site showed no similarity too this motif. Within the intron, a sequence which occurs in several transcription repressing elements (NRE, AGCCTCTC at pos. 122)[53] was found.

A number of viral enhancer motifs could also be discerned. The NF-kB site at position −804 overlaps a sequence found in the adenovirus E2A promoter, defined as a binding site for the transcriptional factor E2aE-Cb[54]. Another consensus sequence found in enhancers of the JC and BK type polyoma viruses as well as in the SV40 enhancer, and in the regulatory regions of several cellular genes, GGGXGGPuPu ("JVC")[55] resides at 110, 349, −326 (reverse) and −256 (reverse).

EXAMPLE 6
Nucleotide Frequency

A high content of C and T nucleotides has been implicated in DNAse hypersensitivity and is found at sites of active transcription in the chromosome[56]. Abundance of the dinucleotide CpG and changes in the methylation pattern of CpG regions have been related to the effect of differentiation mechanisms on gene expression[57], while overall G/C abundance in promoter sequences has been associated with the control of house-keeping genes (e.g., [58-60]). We therefore examined the 5' end of the TNF receptor gene for these features, by computing the content of C/T, G/C and CpG along this region, at a window width 200 nucleotides.

As shown in FIG. 4, a distinct region within this sequence, extending from about nucleotide −400 to −100, has a high content of C and T nucleotides. That region overlaps the one in which the transcription start sites are clustered. A particular C/T rich sequence, GGCCTCCTCCTCC (Nucleotides 478–490 and 501–513 of SEQ ID NO:1), occurs twice, closely upstream to the furthest 5' start site (at nucleotides −332 and −309).

Downstream to the region rich in C and T residues, there is a region with a high CpG content; the highest content occuring in the 5' end of the first intron. An overall abundance of C and G nucleotides was observed from about nucleotide −331 downstream; again, it was highest in the 5' end of the first intron of the p55 gene (nt. 40–200), where the G and C nucleotides constitute together 70% of the sequence.

EXAMPLE 7
Initial Steps Towards Identification of Factors Binding to the Promoter Region A simple way to identify factors which bind to a given sequence is the electrophoretic mobility shift assay (EMSA), which was employed in this case. The 178 bp fragment BglII-EcoRI (corresponding to construct P5 in FIG. 2) was labeled at the 5' end by a fill-in reaction using Klenow Polymerase and $^{32}$P-dCTP. 10,000 cpm of labeled fragment were incubated in with 5 µg total protein of HeLa cell nuclear extract under varying buffer conditions and separated on a 3.5% native acrylamide gel. The experiments demonstrated the following:

1) several minor and one major band were observed, corresponding to potential transcription factors binding to the BglII-EcoRI fragment;
(2) incubation of the nuclear extract with an excess of unlabeled BglII-EcoRI fragment completely abolished binding, indicating that the observed interactions are specific;
(3) addition of non-specific competitor DNA (salmon sperm DNA) reduced background, but did not abolish the appearance of the major band;
(4) salt concentrations of up to 250 mM of Na$^+$ and K$^+$ left binding unaffected, again demonstrating the specific nature of this interaction, as non-specific binding is often reduced or abolished upon an increase in salt concentration;
(5) increase in Mg$^{++}$ concentration up to 10 mM decreased but did not abolish binding to all observed complexes;
(6) identical binding patterns were observed at 20° C. and at 0° C.;
(7) no binding could be observed when cytoplasmic extracts of HeLa cells were used. This demonstrates once more the specific nature of the binding, since active transcription factors are expected to be localized to the nucleus of the cells.

Taken together, these data suggest that at least one factor interacts specifically with the region essential for promoter activity of the p55 TNF receptor upstream gene sequence.

EXAMPLE 8
Purification of Transcription Factors Binding to the Promoter Region Functional motifs in the promoter region can be identified by step-wise deletion of nucleic acid sequence from the 3' and/or 5' end of the promoter by conventional means (Erase-a-Base kit, Promega Corp.). The deleted promoter fragments are then tested for activity. Likewise, internal sequences can be deleted or changed by in vitro mutagenesis or linker scanning[39]. Motifs that bind activating transcription factors are revealed by a loss of promoter activity when deleted or mutated. Conversely, motifs that bind transcription factors which supress promoter activity are identified by mutated or deleted promoter fragments which have increased activity, compared to the wild-type promoter. A detailed analysis of these motifs is then carried out by chemical synthesis of oligonucleotides with the sequence of the original motif, and mutated forms of it. These oligonucleotides are linked to the promoter fragments lacking the corresponding motifs, and the resulting construct is tested for promoter activity. If the original activity is restored, the motif can be regarded as functionally unchanged, i.e., those mutations that have been introduced into the motif, do not interfere with its function. On the other hand, if less promoter activity is observed with a mutated motif, it can be concluded that the nucleotides which were changed compared to the wild-type motif, are essential for its function.

Once a transcription factor binding motif has been identified, the corresponding transcription factor is isolated. For this purpose, extracts from several sources are screened for high expression of that transcription factor. The amount of transcription factor present can be measured by gel shift assays, using the above described oligonucleotides containing the sequence of the functional motif as 5'-end-labeled, ds-DNA probes.

Having identified an abundant source of the transcription factor, the conditions that are required for optimum binding can be defined. Different chemical parameters, such as pH, presence of various mono- and divalent cations, salt concentration and the presence of reducing agents, e.g., DTT or mercaptoethanol are adjusted to achieve this goal.

Having established optimal binding conditions for the transcription factor, purification is carried out by conventional means, e.g., by salt precipitation, phosphocellulose and/or DEAE chromatography. An enriched precipitation of the transcription factor is then purified further on a DNA affinity column, in which the oligonucleotide containing the corresponding motif is bound to an insoluble matrix, and the transcription factor-containing solution is passed over the column under conditions optimal for binding. After washing off contaminants, the purified transcription factor is eluted by conditions which do not allow DNA binding, e.g., pH shift, changed salt concentration, or chelation of divalent salts necessary for DNA binding (usually $Zn^{++}$).

Having purified the transcription factor allows the application of "reverse genetics" on that molecule: protein sequencing, cDNA cloning using degenerated oligonucleotides corresponding to protein sequence and finally, cloning of the gene encoding the transcription factor by screening genomic libraries using the cDNA as a probe.

Having all these tools: genomic clones, cDNA and purified transcription factors, allows to define ways to regulate the activity of the trascription factor by one of the following means: (1) influencing its promoter; (2) influencing its binding to the target in the p55 TNF-R gene promoter; or (3) modulating its activity.

A detailed procedure for (1) is given in Example 9. Methods (2) and (3) can be achieved by screening a large number of drugs for interference with the function of this transcription factor.

EXAMPLE 9
Modulation of Promoter Activity by Specific Sequence Regions

The activity of a promoter can be regulated by scavenging transcription factors which are in short supply. This can be done by expressing multiple copies of the corresponding motifs to which the transcription factors bind. This mechanism has recently been demonstrated by Pai et al.[68], who expressed and amplified the negative promoter domain of the c-myc promoter in the hamster CHO cell line. Following that, the authors observed increased expression of hamster c-myc and the corresponding changes in cell growth and morphology induced by myc protein. Much in the same way, it is possible to amplify promoter regions which activate and enhance promoter activity, and by that decrease the expression of the corresponding protein.

For the p55 TNF-R promoter, either the whole promoter or parts of it which have been identified as negative or positive regulatory domains, can be excised from the promoter sequence by restriction digest or exonuclease deletion of irrelevant sequences. The fragments obtained are then linked to a vector that allows gene amplification, and transfected into a cell line e.g., CHO cells, which allows selection for amplified vector sequences. After selection and amplification, the obtained clones of CHO cells are checked for p55 TNF-R gene expression on the mRNA and protein level. In addition, the function of the receptors is checked by cytotoxicity assay with TNF or with TNF mimicking antibodies which cross-react with the hamster receptor (e.g., the α mouse p55 antibodies).

Having established promoter regions which, upon amplification in this system, modulate the activity of the p55 receptor, these same regions are introduced into cells which do not allow selection for amplified gene products in two ways:

1) coexpression of promoter regions linked to a vector which contains a viral origin of replication (e.g., SV40 or EBNA), with a vector which expresses T antigen (of SV40), or EBNA antigen. This allows the replication of high numbers of episomal copies of the introduced promoter fragment in the nucleus of the target cell and thus mimicks the effect of DNA amplification of integrated sequences.

2) chemical synthesis of a ds oligonucleotide comprising the promoter domain and application of sufficient amounts of that oligonucleotide to cells makes it likewise possible to scavenge the corresponding transcription factors and thus influence promoter activity. The chemistry of the oligonucleotides has to be changed in order to (a) make the oligonucleotide more lipophilic, so that it can pass the cytoplasmic membrane, and (b) enhance its stability in order to minimize degradation. This is done by conventional means, e.g., by using phosphothioate-coupled oligonucleotides.

REFERENCES

1. Tracey, J. T. et al. (1987) Nature, 330:662–664.
2. Piquet, P. F. et al. (1987) J.Exp.Med., 166:1280–89.
3. Beutler, B. and Cerami, C. (1987) NEJM, 316:379–385.
4. Hohmann, H.-P. et al. (1989) J.Biol.Chem., 264:14927–14934.
5. Engelmann, H. et al. (1990) J.Biol.Chem., 265:1531–1536.
6. Brockhaus, M. et al. (1990) Proc.Natl.Acad.Sci. USA, 87: 3127–3131.

7. Loetscher, H. et al. (1990) Cell, 61:351–359.
8. Schall, T. J. et al (1990) Cell, 61:361–370.
9. Nophar, Y. et al. (1990) EMBO J., 9:3269–3278.
10. Smith, C. A. et al. (1990) Science, 248:1019–1023.
11. Heller, R. A. et al. (1990) Proc.Natl.Acad.Sci.USA, 87: 6151–6155.
12. Aggarwal, B. B. et al. (1985) Nature, 318:66–667.
13. Israel, S. et al. (1986) Immunol. Lett., 12:217–224.
14. Tsujimoto, M. et al. (1986) Biochem.Biophys.Res.Commun., 137: 1094–1100.
15. Ruggiero, V. J. et al. (1986) J.Immunol., 136:2445.
16. Holtmann, H. and D. Wallach (1987) J. Immunol., 139:1161–1167.
17. Ding, A. H. et al. (1989) J.Biol.Chem., 264:3924.
18. Porteu, F. and Nathan, C. (1990) J.Exp.Med., 17:599–607.
19. Porteu, F. et al. (1991) J.Biol.Chem., 266:18846.
20. Ware, C. F. et al. (1991) J.Immunol., 147:4229.
21. Erikstein, B. K. et al. (1991) Eur.J.Immunol., 21:1033.
22. Winzen, R. et al. (1992) J.Immunol., 148:3454.
23. Espevik, T. et al. (1990) J.Exp.Med., 171:415–426.
24. Engelmann, H. et al. (1990) J.Biol.Chem., 265:14497–14504.
25. Thoma, B. et al. (1990) J.Exp.Med., 172:1019–1023.
26. Tartaglia, L. A. et al. (1991) Proc.Natl.Acad.Sci.USA, 88:9292–6.
27. Gehr, G. et al. (1992) J.Immunol., 149:911.
28. Heller, R. A. et al. (1992) Cell, 70:47.
29. Brakebusch, C. et al. (1992) ENBO J., 11:943–950.
30. Vandenabeele, P. et al. (1992)J.Exp.Med., 176:1015.
31. Gey, G. O. et al. (1952) Cancer Res., 12:254–265.
32. Littlefield, J. W. (1964) Nature, 203:1142.
33. Sundstrom, C. and Nillson, K. (1976) Int.J.Cancer, 17: 565–577.
34. Derre, J. et al. (1991) Hum.Genet., 87:231–233.
35. Benech, P. et al. (1987) Mol.Cell.Biol., 7:4498–4504.
36. Sanger, F. et al. (1977)Proc.Natl.Acad.Sci.USA, 74:5463–5467.
37. Maniatis, T. et al. (1982) *Molecular Cloning: A Laboratory Manual*, Cold Spring Harbor Laboratory Press, Cold Spring Harbor, N.Y.
38. McDonald, R. J. et al. (1987) Meth.Enzymol., 152:223–226.
39. Sambrook, J. et al. (1989) *Molecular Cloning: A Laboratory Manual*, Cold Spring Harbor Laboratory Press, Cold Spring Harbor, N.Y.
40. Fuchs, P. et al. (1992) Genomics, 13:219–224.
41. Huang, D. H. et al. (1988) J.Biol.Chem., 263:12596–12601.
42. Morgan, W. D. et al. (1987) Mol.Cell.Biol., 7:1129–1138.
43. McKnight, S. and Tjian, R. (1986) Cell, 46:795–805.
44. Devereux, J. et al. (1984) Nucleic Acids Res., 12:387–395.
45. Lenardo, M. J. and Baltimore, D. (1989) Cell, 58:227–229.
46. Imagawa, M. et al. (1987) Cell, 51:251–260.
47. Distel, R. et al. (1987) Cell, 49:835–844.
48. Greene, J. M. et al. (1987) Mol.Cell.Biol., 7:3646–3655.
49. Jones, K. A. and Tjian, R. (1985) Nature, 317:179–182.
50. Briggs, M. et al. (1986) Science, 234:47–52.
51. Johnson, A. C. et al. (1988) Mol.Cell.Biol., 8:4174–4184.
52. Smale, S. T. and Baltimore, D. (1989) Cell, 57:103–113.
53. Baniahmad, A. et al. (1987) EMBO J., 6:2297–2303.
54. Jones, N. C. et al. (1988) Genes Dev., 2:267–281.
55. Martin, J. D. et al. (1985) J.Virol., 53:306–311.
56. Larsen, A. and Weintraub, H. (1982) Cell, 29:609–622.
57. Bird, A. P. (1986) Nature, 321:209–213.
58. Sauerwald, A. et al. (1990) J.Biol.Chem., 265:14932–14937.
59. Srivastava, M. et al. (1990) J.Biol.Chem., 265:14922–14931.
60. Sehgal, A. et al. (1988) Mol.Cell.Biol., 8:3160–3167.
61. Melton, D. W. et al. (1984) Proc.Natl.Acad.Sci.USA, 81:2147.
62. Ishii, S. et al. (1985) Science, 230:2592.
63. Ye, K., Dinarello, C. A. and Clark, B. D. (submitted for publication).
64. Giroir, B. P. et al. (1992) Proc.Natl.Acad.Sci.USA, 89: 4864–4868.
65. Nedospasov, S. A. et al. (1986) Cold Spring Harbor Symp. Ouant. Biol., 51:611.
66. Turetskaya, R. L. et al. (1992) in: B. B. a. V. Aggarwal, J. (ed.) *Tumor Necrosis Factor: Structure, Function and Mechanism of Action*, Marcel Dekker, Inc., New York 56, pp. 35–60.
67. Lowenthal, J. W. et al. (1989) Proc.Natl.Acad.Sci.USA, 86: 2331–2335.
68. Pai et al. (1992) J. Biol.Chem., 267:12428–31.

What is claimed is:

1. An isolated DNA promoter sequence capable of promoting the expression of the human p55 TNF-R gene, said promoter sequence being all or part of nucleotides 1–809 of SEQ ID NO:1, but containing not less than nucleotides 456–524 of SEQ ID NO:1.

2. An isolated DNA promoter sequence capable of promoting the expression of the human p55 TNF-R gene, consisting essentially of nucleotides 456–524 of SEQ ID NO:1.

3. A sequence according to claim 1, said sequence being all or part of nucleotides 1–603 of SEQ ID NO:1, but containing not less than nucleotides 456–524 of SEQ ID NO:1.

4. A sequence according to claim 3, said sequence being all or part of nucleotides 426–603 of SEQ ID NO:1, but containing not less than nucleotides 456–524 of SEQ ID NO:1.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:

(A) LENGTH: 1239 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 810..848

(xi) SEQUENCE DESCRIPTION: SEQ ID NO:1:

```
GATCAGTAAA TTCCCAAGAA AGAGGGAGAC TAGGAGGCTA GTGAAGAACT CTGGAGTAAA    60

GGGGAGGATT ACTAAGGGAC ATGGAGTACC TATCATGTGT CGGACGCTTA TCTATATCTC   120

TCCCATCTGA ACAAATCCTT ACAGGAACCC AGGAGACAG GTTATCTCCA CTCTGCAAAT   180

TGGAAAACAG ATCCAGACAG GTTCAGTTAT GTGTCTGAGA AGTTCATTTG TGTGTCCAAG   240

ACACATTCTT AGCTAAAAAG CTAAGCATTC TGAATTGGAA CCCAGAGAAT TTGACTCCCA   300

GACTCTGGAT CTTTTCACTG CTGTGATCCA TCTGGGAAAG CTAGTGATG TGGGCAAGGG   360

CTTATTGCCC CTTGGTGTTT GGTTGGGAGT GGTCGGATTG GTGGGTTGGG GGCACAAGGC   420

AGCCAGATCT GGGACTCCTG TGCTTGTGAC TGGACTACAA AGAGTTAAAG AACGTTGGGC   480

CTCCTCCTCC CGCCTCCTGT GGCCTCCTCC TCCAGCTCTT CCTGTCCCGC TGTTGCAACA   540

CTGCCTCACT CTTCCCCTCC CACCTTCTCT CCCCTCCTCT CTGCTTTAAT TTTCTCAGAA   600

TTCTCTGGAC TGAGGCTCCA GTTCTGGCCT TTGGGGTTCA AGATCACTGG GACCAGGCCG   660

TGATCTCTAT GCCCGAGTCT CAACCCTCAA CTGTCACCCC AAGGCACTTG GACGTCCTG   720

GACAGACCGA GTCCCGGGAA GCCCCAGCAC TGCCGCTGCC ACACTGCCCT GAGCCCAAAT   780

GGGGGAGTGA GAGGCCATAG CTGTCTGGC ATG GGC CTC TCC ACC GTG CCT GAC   833
                                Met Gly Leu Ser Thr Val Pro Asp
                                  1               5

CTG CTG CTG CCA CTG GTGAGACCAG GGACAAAGGG AAGAGTGGGC TGGTGGGCGA    888
Leu Leu Leu Pro Leu
      10

GGCACCTTCC GGCTGGCGTG GGCCCTCTCC GGGAGGGGGC CGAGCCTCTC CTGCCCGGGC   948

CTGGTCCTGG CGCCAGTCAG GCCTGCAGGT CCTAACCTCA GCCACTGCCA GTGTGGGGTT  1008

CCCCATTCAT CCGCCTTTTG GAGTAGGGGC TGCGCTGAGG CAGGGGAATG GGAGAAGTTT  1068

GAAAGGGAGA GAGTAAAAGG AAGCCCTGGC CCCTGACAGC GGTGGAAGTT TGTGGGCGGC  1128

CAAGGGAATG TGGGCAGGAG GTAGGCCCAG GGTGGGGCAG ATTTGGCGGG GAAAAGAAGG  1188

GAGTGGGAGT AGGAAGATTA GCGCTCGGGG AGTCCAGACG GTTCTGAATT C           1239
```

(2) INFORMATION FOR SEQ ID NO:2:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Leu Ser Thr Val Pro Asp Leu Leu Leu Pro Leu
  1               5                  10
```

(2) INFORMATION FOR SEQ ID NO:3:

(i) SEQUENCE CHARACTERISTICS:
        (A) LENGTH: 23 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GGTGACAGTT GAGGGTTGAG ACT                                        23

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CAATTCAGAA TGCTTAGCTT T                                          21

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGTGACAGTT GAGGGTTGAG ACT                                        23

(2) INFORMATION FOR SEQ ID NO:6:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

KRGGCGKRRY                                                       10

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

ATTCTGGGAG AC                                                    12